United States Patent
De Mesmaeker et al.

(12) 
(10) Patent No.: US 6,255,251 B1
(45) Date of Patent: Jul. 3, 2001

(54) ISOXAZOLE DERIVATIVES AND THEIR USE AS HERBICIDES

(75) Inventors: Alain De Mesmaeker, Kaenerkinden (CH); Jürgen Schaetzer, Rheinfelden (DE); Walter Kunz, Oberwil (CH)

(73) Assignee: Syngenta Crop Protection, Inc., Greensboro, NC (US)

( * ) Notice: Subject to any disclaimer, the term of this patent is extended or adjusted under 35 U.S.C. 154(b) by 0 days.

(21) Appl. No.: 09/677,570

(22) Filed: Oct. 2, 2000

Related U.S. Application Data

(63) Continuation of application No. PCT/EP99/02223, filed on Mar. 31, 1999.

(30) Foreign Application Priority Data

Apr. 2, 1998 (CH) .................................... 0785/98

(51) Int. Cl.⁷ .......................... A01N 43/80; C07D 261/10
(52) U.S. Cl. .......................... 504/271; 548/243
(58) Field of Search .............................. 548/243; 504/271

(56) References Cited

U.S. PATENT DOCUMENTS 5,863,865 * 1/1999 Lee et al. .............. 504/271

FOREIGN PATENT DOCUMENTS

| 2056044 | 5/1992 | (CA) . |
| 2101105 | 1/1994 | (CA) . |
| 0487357 | 5/1992 | (EP) . |
| 0580439 | 1/1994 | (EP) . |
| WO97/43270 | 11/1997 | (WO) . |

\* cited by examiner

*Primary Examiner*—Deborah C. Lambkin
*Assistant Examiner*—Andrea M D'Souza
(74) *Attorney, Agent, or Firm*—William A. Teoli, Jr.

(57) ABSTRACT

Compounds of formula 1

(I)

wherein $R_1$ and $R_2$ are independently $C_1$–$C_8$alkyl, are suitable for use as herbicides.

5 Claims, No Drawings

ISOXAZOLE DERIVATIVES AND THEIR USE AS HERBICIDES

This application is a continuation of PCT/EP99/02223 filed Aug. 31, 1999.

This is a continuation of International Application No. PCT/EP99/02223, filed Mar. 31, 1999, the contents of which are incorporated herein by reference.

The present invention relates to new, herbicidally effective isoxazole derivatives, to compositions comprising said compounds, and to the use thereof for controlling weeds, in particular in crops of cultivated plants or for inhibiting plant growth.

Isoxazole derivatives with a herbicidal effect are described for example in WO 97/43270. The active ingredients disclosed therein, however, cannot always satisfy requirements with regard to potency and spectrum of action. There is thus a need for active ingredients with improved herbicidal characteristics. It has now been found that isoxazole derivatives with a specific substitution pattern possess outstanding herbicidal characteristics.

Accordingly, the invention relates to compounds of formula I

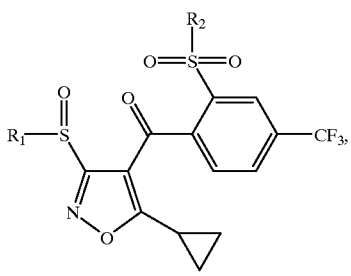

wherein $R_1$ and $R_2$ are independently $C_1$–$C_8$alkyl.

The alkyl groups occurring in the definitions of the substituents may be straight-chain or branched and are typically methyl, ethyl, n-propyl, isopropyl, n-butyl, sec-butyl, isobutyl, tert-butyl and the isomers pentyl, hexyl, heptyl and octyl groups.

A compound of formula 1, wherein $R_1$ and $R_2$ are methyl, is preferred.

Compounds of formula I are prepared in a manner similar to that with known processes. Such manufacturing processes are described for example in WO 97/43270.

The compounds of formula I or compositions containing them may be used according to this invention by all standard methods of application used in agriculture, including preemergence application, postemergence application and seed dressing, as well as by different methods and techniques such as controlled release. For controlled release, a solution of the herbicide is applied to mineral granular carriers or to polymerized granules (urea/formaldehyde) and then dried. A coating can then be additionally applied (coated granules) that allows the herbicide to be released at a controlled rate over a specific period of time.

The compounds of formula I may be used as herbicides in unmodified form, i.e. as obtained in the synthesis. Preferably they are processed in conventional manner with the auxiliary agents customarily employed in formulation technology, e.g. to emulsifiable concentrates, directly sprayable or dilutable solutions, dilute emulsions, wettable powders, soluble powders, dusts, granulates or microcapsules. Such formulations are described, for example, in WO 97/34485 on pages 9 to 13. As with the type of agents, the methods of application such as spraying, atomizing, dusting, wetting, scattering or pouring, are selected in accordance with the intended objectives and the prevailing circumstances.

The formulations, i.e. the agents, preparations, or compositions containing the compound of formula I or at least one compound of formula I and usually one or more than one liquid or solid formulation assistant, are prepared in known manner, e.g. by homogeneously mixing and/or grinding the herbicide with said formulation auxiliaries, typically solvents or solid carriers. Surface-active compounds (surfactants) may additionally be used for preparing the formulations. Examples of solvents and solid carriers are described in WO 97/34485 on page 6.

Depending on the herbicide of formula I to be formulated, suitable surface-active compounds are non-ionic, cationic and/or anionic surfactants and surfactant mixtures having good emulsifying, dispersing and wetting properties.

Examples of suitable anionic, non-ionic, and cationic surfactants are listed in WO 97/34485 on pages 7 and 8.

Also the surfactants customarily employed in the art of formulation and described, inter alia, in "Mc Cutcheon's Detergents and Emulsifiers Annual" MC Publishing Corp., Ridgewood N.J., 1981, Stache, H., "Tensid-Taschenbuch" (Handbook of Surfactants), Carl Hanser Verlag, MunichNienna, 1981, and M. and J. Ash, "Encyclopedia of Surfactants", Vol I–III, Chemical Publishing Co., New York, 1980–81 are suitable for manufacture of the herbicides according to the invention.

The herbicidal compositions will as a rule contain from 0.1 to 99% by weight, preferably from 0.1 to 95% by weight, of herbicide, from 1 to 99.9% by weight, preferably from 5 to 99.8% by weight, of a solid or liquid adjuvant, and from 0 to 25% by weight, preferably from 0.1 to 25% by weight, of a surfactant. Whereas it is preferred to formulate commercial products as concentrates, the end user will normally use dilute formulations. The compositions may also contain further ingredients, such as: stabilisers, e.g. where appropriate epoxidized vegetable oils (epoxidized coconut oil, rapeseed oil, or soybean oil); antifoams, typically silicone oil; preservatives; viscosity regulators; binders; and tackifiers; as well as fertilizers or other chemical agents.

The compounds of formula I are usually applied with success to the plants or the locus thereof in concentrations of 0.001 to 4 kg/ha, especially 0.005 to 2 kg/ha. The concentration required to achieve the desired action can be determined by experimentation. It will depend on the type of action, the development stage of the cultivated plant and of the weed, as well as on the application (locus, time, method), and as a result of these variables can vary over a wide range.

The compounds of formula I have excellent herbicidal and growth inhibiting properties, which make them suitable for application in crops of cultivated plants, especially in cereals, cotton, soybeans, sugar beet, sugar cane, plantations, rape, maize, and rice, and for the non-selective control of weeds. Crops will also be understood as meaning those crops that have been made tolerant to herbicides or classes of herbicides by conventional breeding or genetic engineering methods. The weeds to be controlled may be monocot as well as dicot weeds, typically Stellaria, Nasturtium, Agrostis, Digitaria, Avena, Setaria, Sinapis, Lolium, Solanum, Echinochloa, Scirpus, Monochoria, Sagittaria, Bromus, Alopecurus, Sorghum halepense, Rottboellia, Cyperus, Abutilon, Sida, Xanthium, Amaranthus, Chenopodium, lpomoea, Chrysanthemum, Galium, Viola, and Veronica.

The invention is illustrated by the following non-limitative Examples.

PREPARATIVE EXAMPLES

Example H1
Preparation of 1-cyclopropyl-3-(2-methylsulfanyl-4-trifluoromethylphenyl)-propane-1,3-dione:

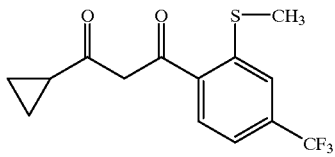

74.8 g (1.715 mol) NaH (55% in oil) is washed three times with n-pentane. Then 400 ml tetrahydrofuran is added, and to the suspension thus obtained a solution of 93.6 g cyclopropylmethylketone in 200 ml tetrahydrofuran is added drop by drop over a period of 45 minutes at a temperature of 30° C. The reaction mixture is then agitated for one hour at a temperature of 30° C. and for two hours at a temperature of 45° C. When no further development of hydrogen is discernible, the mixture is cooled to a temperature of 20° C., and a solution of 116 g (0.46 mol) 2-thiomethyl-4-trifluoromethyl-benzoic acid methyl ester in 250 ml THF is added drop by drop. After this addition, the mixture is agitated for 18 hours at a temperature of 20° C. The reaction mixture is then cooled to a temperature of 0° C., diluted with 1000 ml ether, and carefully treated with diluted hydrochloric acid until pH 1 is attained. Through the addition of a further 300 ml ether and 100 ml water, a clear solution is obtained. After washing with water and concentrated aqueous sodium chloride solution, the organic phase is separated off and then dried over sodium sulfate. The oily raw product is treated with n-pentane, which yields 106 g crystalline 1-cyclopropyl-3-(2-methylsulfanyl-4-trifluoromethylphenyl)propane-1,3-dione with a melting point of 62–63° C.

Example H2
Preparation of 1-cyclopropyl-3-(2-methanesulfonyl-4-trifluoromethylphenyl)-propane-1,3-dione:

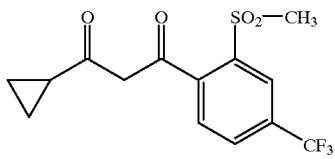

102.8 g (0.34 mol) 1-Cyclopropyl-3-(2-methylsulfanyl-4-trifluoromethylphenyl)propane-1,3-dione is dissolved in 800 ml dichloromethane and then cooled to a temperature of −20° C. Over a period of 45 minutes, 184.4 g (70%, 0.75 mol) m-chloroperbenzoic acid is then added in portions. After this addition, the mixture is agitated for 1.5 hours at a temperature of −15 to −10° C. The solution is then diluted with a further 700 ml dichloromethane and agitated for 18 hours at a temperature of 0 to 5° C. After the precipitate has been filtered off, the dichloromethane phase is washed successively with aqueous NaHSO$_3$ solution, aqueous NaHCO$_3$ solution, concentrated aqueous sodium chloride solution and water, and then dried over magnesium sulfate. After the magnesium sulfate has been filtered off and the solvent evaporated, the residue is digested in ether. This yields 79 g crystalline 1-cyclopropyl-3-(2-methanesulfonyl-4-trifluoromethylphenyl)propane-1,3-dione with a melting point of 123–125° C.

Example H3
Preparation of 2-(bis-methylsulfanylmethylene)-1-cyclopropyl-3-(2-methanesulfonyl-4-trifluoromethylphenyl)propane-1,3-dione:

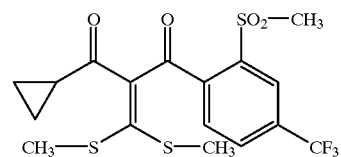

25.9 g (0.078 mol) 1-Cyclopropyl-3-(2-methanesulfonyl-4-trifluoromethylphenyl)propane-1,3-dione is dissolved under an argon atmosphere in 180 ml DMF and then cooled to a temperature of −3° C. Then 56.3 g KF (0.124 mol, 40% on Al$_2$O$_3$) is added in portions followed by 7.5 ml (0.124 mol) carbon disulfide drop by drop. After 2 hours of agitation at a temperature of 0° C., 13.5 ml (0.217 mol) methyl iodide is added drop by drop while cooling. The yellow suspension thus obtained is then heated slowly to a temperature of 20° C. and agitated for 18 hours. On completion of the reaction, surplus KF/Al$_2$O$_3$ is filtered off and the solvent distilled off in a vacuum. The residue is taken up in ethyl acetate and washed with water and concentrated aqueous sodium chloride solution. After the organic phase has been separated off, it is dried over sodium sulfate. A resin is obtained as raw product, which is subjected to flash chromatography on silica gel with ethyl acetate/hexane (1:4) as eluent. This yields 14.3 g crystalline 2-(bis-methylsulfanylmethylene)-1-cyclopropyl-3-(2-methanesulfonyl-4-trifluoromethylphenyl)propane-1,3-dione with a melting point of 137–139° C.

Example H4
Preparation of 5-cyclopropyl-3-methylsulfanyl-4-(2-methanesulfonyl-4-trifluoromethylbenzoyl)isoxazole:

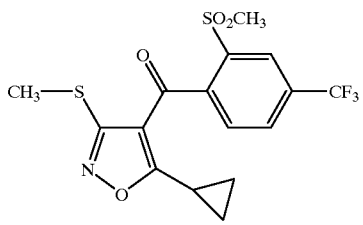

To a solution of 12.5 g (28.4 mmol) 2-(bis-methylsulfanylmethylene)-1-cyclopropyl-3-(2-methanesulfonyl-4-trifluoromethylphenyl)propane-1,3-dione in 80 ml dichloromethane, 140 ml each of ethanol, 2.82 g (39.8 mmol) hydroxylamine hydrochloride and 3.4 g (41.2 mmol) anhydrous sodium acetate is successively added. The reaction mixture is then agitated for 48 hours at a temperature of 20° C. Then 50 ml dichloromethane, 50 ml ethanol, 1.4 g hydroxylamine hydrochloride and 1.7 g anhydrous sodium acetate are added, and the mixture is agitated for a further 3 days at 20° C. The reaction mixture is subsequently heated to a temperature of 30° C., and 2.8 g hydroxylamine hydrochloride and 3.4 g sodium acetate are added. After 18 hours' agitation at a temperature of 30° C., the solvents are distilled off and the residue taken up in 300 ml ethyl acetate. The organic phase is washed twice with water and once with concentrated aqueous sodium chloride solution. After the organic phase has been dried over sodium sulfate, it is treated with activated charcoal, filtered and evaporated to dryness. After recrystallization from a little diisopropylether, 10.7 g 5-cyclopropyl-3-methylsulfanyl-4-(2-methanesulfonyl-4-trifluoromethylbenzoyl)isoxazole is obtained in the form of crystalline solid matter with a melting point of 145–146° C.

Example H5

Preparation of 5-cyclopropyl-3-methylsulfinyl-4-(2-methanesulfonyl-4-trifluoromethylbenzoyl)isoxazole:

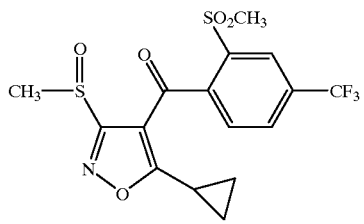

1.0 g (2.5 mmol) 5-Cyclopropyl-3-methylsulfanyl-4-(2-methanesulfonyl-4-trifluoromethylbenzoyl)isoxazole is dissolved in 12 ml dichloromethane. The solution is then cooled to a temperature of −5° C., and 0.62 g (70%, 2.5 mmol) m-chloroperbenzoic acid is added in portions. After 18 hours' agitation at a temperature of 0 to 5° C., the reaction mixture is diluted with dichloromethane and the resulting precipitate filtered off. The dichloromethane phase is successively extracted with 5% aqueous $NaHCO_3$ solution, twice with water and 15% aqueous sodium chloride solution. After the organic phase has been separated off, it is dried over magnesium sulfate. The raw product obtained is subjected to flash chromatography on silica gel using ethyl acetate/hexane (first 1:1 then 2:1) as eluent. After stirring in a little diisopropylether, 0,8 g of 5-cyclopropyl-3-methylsulfinyl-4-(2-methanesulfonyl-4-trifluoromethylbenzoyl)isoxazole is obtained in the form of crystals with a melting point of 153–155° C. $^1$H-NMR ($CDCl_3$, ppm): 0.96–1.16 (m, 2H), 1.2–1.36 (m, 1H), 1.32–1.4 (m, 2H), 3.12 (s, 3H), 3.32 (s, 3H), 7.72 (d, 1H), 8.05 (d, 1H), 8.41 (s, 1H).

The compounds in Table 1 are obtained in a manner analogous to that described in the preparative examples.

TABLE 1

Compounds of formula 1:

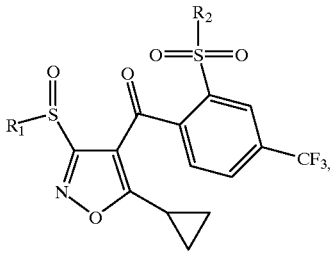

(I)

| Comp. no. | $R_1$ | $R_2$ | Phys. data |
|---|---|---|---|
| 1.001 | $CH_3$ | $CH_3$ | m.p. 153–155° C.; |
| 1.002 | $CH_3$ | $C_2H_5$ | |
| 1.003 | $CH_3$ | $i-C_3H_7$ | |
| 1.004 | $CH_3$ | $n-C_3H_7$ | |
| 1.005 | $CH_3$ | $n-C_4H_9$ | |
| 1.006 | $C_2H_5$ | $CH_3$ | |

TABLE 1-continued

Compounds of formula 1:

| Comp. no. | $R_1$ | $R_2$ | Phys. data |
|---|---|---|---|
| 1.007 | $C_2H_5$ | $C_2H_5$ | |
| 1.008 | $C_2H_5$ | $i-C_3H_7$ | |
| 1.009 | $i-C_3H_7$ | $CH_3$ | |
| 1.010 | $i-C_3H_7$ | $C_2H_5$ | |
| 1.011 | $i-C_3H_7$ | $i-C_3H_7$ | |
| 1.012 | $n-C_3H_7$ | $CH_3$ | |
| 1.013 | $n-C_3H_7$ | $C_2H_5$ | |
| 1.014 | $n-C_3H_7$ | $n-C_3H_7$ | |
| 1.015 | $n-C_4H_9$ | $CH_3$ | |
| 1.016 | $n-C_4H_9$ | $C_2H_5$ | |
| 1.017 | $n-C_4H_9$ | $n-C_3H_7$ | |
| 1.018 | $i-C_4H_9$ | $CH_3$ | |
| 1.019 | $i-C_4H_9$ | $C_2H_5$ | |
| 1.020 | $i-C_4H_9$ | $i-C_3H_7$ | |
| 1.021 | $n-C_4H_9$ | $n-C_4H_9$ | |

Biological Examples

Example B1

Preemergence Herbicidal Action

Monocot and dicot test plants are sown in standard soil in plastic pots. Immediately after sowing, the plants are sprayed at a concentration of 2 kg active ingredient/ha with an aqueous suspension of the test compound prepared from a 25% wettable powder (Example F3, b)) according to WO 97/34485) or an emulsion of the test compound prepared from a 25% emulsifiable concentrate (Example F1 c)) (500 l of water/ha). The test plants are then cultivated in the greenhouse under optimum conditions. The test is evaluated 3 weeks later on a rating scale of 1–9 (1=total damage, 9=no action). Ratings of 1 to 4 (especially of 1 to 3) denote good to very good herbicidal action. In this test, the compounds of formula I exhibit a good herbicidal action.

The same results are obtained by formulating the compounds of formula I in accordance with Examples F2 and F4 to F8 as described in WO 97/34485.

Example B2

Comparison of the herbicidal action of compound no. 1.001 according to the invention with the structurally most closely comparable compound from the state of the art (compound no. 14 from page 15 of WO 97/43270).

(Compound no. 1.001 according to present invention)

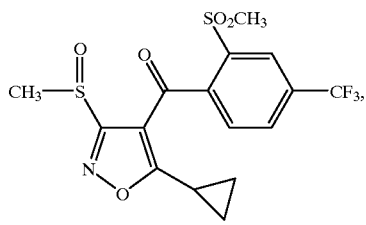

Compound no. 14 from page 15 of WO 97/43270

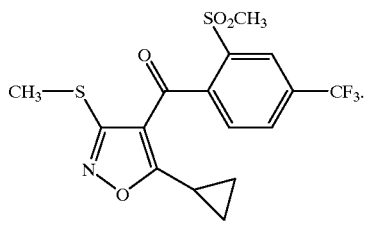

Postemergence Herbicidal Action

Monocot and dicot test plants are sown under greenhouse conditions in standard soil in plastic pots. At the 4 to 6-leaf stage, the plants are sprayed at a concentration of 60 kg active ingredient/ha with an aqueous suspension of the test compound prepared from a 25% wettable powder (Example F3, b) according to WO 97/34485) or an emulsion of the test compound prepared from a 25% emulsifiable concentrate (Example F1 c)) (500 l of water/ha). The test is evaluated after 3 weeks on a rating scale of 1 to 9 (1=total damage, 9 no action). Ratings of 1 to 4 (especially of 1 to 3) denote good to very good herbicidal action. The results are shown in Table B1.

TABLE B1

Post-emergent herbicidal action of compound no. 1.001 in comparison with compound no. 14 from the state of the art:

| Test plant: | Compound no. 1.001 | Compound no. 14 from the state of the art |
| --- | --- | --- |
| Avena | 3 | 5 |
| Setaria | 3 | 4 |
| Panicum | 3 | 5 |
| Sorghum | 4 | 7 |
| Echinochloa | 2 | 4 |
| Rottboellia | 3 | 8 |
| Euphorbia | 3 | 4 |
| Sida | 3 | 4 |
| Abutilon | 2 | 4 |

TABLE B1-continued

Post-emergent herbicidal action of compound no. 1.001 in comparison with compound no. 14 from the state of the art:

| Test plant: | Compound no. 1.001 | Compound no. 14 from the state of the art |
| --- | --- | --- |
| Xanthium | 2 | 4 |
| Ipomoea | 4 | 7 |
| Veronica | 3 | 6 |

Table B1 shows that compound No. 1.001 according to the invention exerts a substantially better herbicidal action on weeds than the compound from the state of the art. This enhanced effect was not to be expected on the basis of the structural similarity of these compounds.

The same results are obtained by formulating compound no. 1.001 in accordance with Examples F2 and F4 to F8 as described in WO 97/34485.

What is claimed is:

1. Compounds of formula I

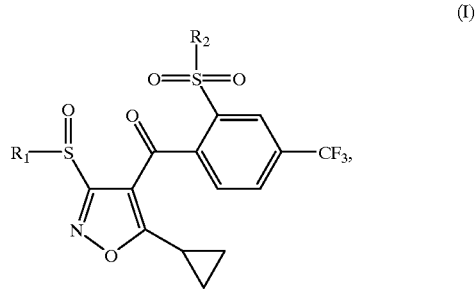

(I)

wherein $R_1$ and $R_2$ are independently $C_1$–$C_8$alkyl.

2. A compound of formula I according to claim 1 wherein $R_1$ and $R_2$ are methyl.

3. A herbicidal and plant growth inhibiting composition, which comprises a herbicidally effective amount of the compound of formula I and an inert carrier.

4. A method of controlling or inhibiting undesirable plant growth, which comprises treating the plants or the locus thereof with a herbicidally effective amount of a compound of formula I.

5. A method of controlling or inhibiting undesirable plant growth, which comprises treating the plants or the locus thereof with a herbicidally effective amount of a composition according to claim 3.

* * * * *